United States Patent [19]
Cordon et al.

[11] 3,955,942
[45] May 11, 1976

[54] ABRASIVE AGGLOMERATES OF ABRASIVE SUBPARTICLES AND BINDER MATERIAL

[75] Inventors: Martin Cordon, Highland Park; Brian J. Pintenich, Piscataway, both of N.J.

[73] Assignee: Colgate-Palmolive Company, New York, N.Y.

[22] Filed: Apr. 4, 1974

[21] Appl. No.: 457,934

Related U.S. Application Data

[60] Division of Ser. No. 242,964, April 11, 1972, Pat. No. 3,803,301, which is a continuation-in-part of Ser. No. 149,786, June 3, 1971, abandoned.

[52] U.S. Cl. .............................. 51/295; 51/298 R; 51/306; 424/49
[51] Int. Cl.² ...................... A61K 7/16; B24D 3/30; B24D 3/32
[58] Field of Search ............. 51/306, 295, 298, 309; 424/49

[56] References Cited
UNITED STATES PATENTS

| | | | |
|---|---|---|---|
| 2,194,472 | 3/1940 | Jackson | 51/298 |
| 2,216,728 | 10/1940 | Benner et al. | 51/298 |
| 3,060,098 | 10/1962 | Gershon | 51/309 |
| 3,116,574 | 1/1964 | Ciesielski | 51/295 |
| 3,151,027 | 9/1964 | Cooley | 51/298 |

*Primary Examiner*—Donald J. Arnold
*Attorney, Agent, or Firm*—Robert L. Stone; Murray M. Grill; Herbert S. Sylvester

[57] ABSTRACT

Toothpaste formulations having dispersed therein an invisible abrasive material and visible abrasive agglomerates are disclosed. The abrasive agglomerates comprise subparticles of hard abrasive materials (Moh hardness of at least about 5) joined together by a binding agent material, and provide increased cleaning and polishing characteristics as well as an attractive speckled appearance to the toothpaste formulation.

8 Claims, 3 Drawing Figures

ABRASIVE AGGLOMERATES OF ABRASIVE SUBPARTICLES AND BINDER MATERIAL

RELATED APPLICATION

This is a division of Application Ser. No. 242,964 filed Apr. 11, 1972, now U.S. Patent 3,803,301, patented Apr. 4, 1974, which is a continuation-in-part of Application Ser. No. 149,786 filed June 3, 1971, now abandoned.

The invention relates to aesthetically pleasing dentifrice formulations having improved cleaning and polishing characteristics. According to one aspect, the invention provides a clear or translucent toothpaste having dispersed therein visible agglomerate particles, each of which comprises a plurality of subparticles of a hard abrasive material held together by a binding agent. For visual effect and to provide aesthetically pleasing characteristics, the visible agglomerates preferably contrast with the color of the toothpaste to provide a speckled effect.

Hard abrasive materials, as contemplated by the invention, include those inorganic, mineral like substances that are well known for their abrasive properties and have been used for many years as industrial polishing agents. Such materials are characterized by a hardness on the Moh scale of between about 5 and 10 (the maximum value), preferably from about 6 to 8.

The primary function of an abrasive substance in formulations intended for use in the oral cavity is to remove various deposits, including pellicle film, from the surface of the teeth. Pellicle film is a tightly adherent film which often contains brown or yellow pigments and imparts an unsightly appearance to the teeth. A further desirable function of dental abrasive agents is to provide a cosmetic effect by polishing the surface of the teeth. An advantageous abrasive material for incorporation into toothpaste formulations should maximize film removal and polishing without causing undue abrasion to the oral hard tissues, particularly dentin.

Dentin is a substantially softer tissue than enamel and is exposed in the mouths of individuals with gingival recession. In evaluating the suitability of an abrasive material for use in a toothpaste, its abrasiveness towards dentin tissues is a special consideration. An abrasive material having a high cleaning and polishing effect on enamel tissue but which also abrades and removes substantial amounts of dentin tissue would not be desirable for use in toothpaste formulations.

A primary advantage of the present invention is to provide a visually clear or translucent gel toothpaste that imparts excellent cleaning and polishing characteristics to the enamel surface of the teeth with a minimum amount of abrasion to the more vulnerable dentin tissues. The toothpaste formulations of the invention include a combination of abrasive materials to accomplish the desired effect. As more particularly described hereinafter, a clear gel toothpaste is provided containing a primary abrasive material that is invisible in the gel vehicle and a secondary abrasive material that is present in the form of visible agglomerates of hard abrasive sub-particles dispersed in the gel vehicle is provided. In addition to providing a significant cleaning and polishing improvement to the toothpaste without a significant increase in dentin abrasion, the visisble abrasive particles can provide an attractive speckled effect to the toothpaste.

Visually clear gel toothpastes, although aesthetically attractive to the consumer, have presented substantial problems with regard to incorporating abrasive agents therein. When conventional dental abrasive agents are added to a visually clear gel vehicle, the gel usually becomes cloudy or opaquish which tends to be undesirable from an aesthetic viewpoint. Abrasive ingredients having a refractive index substantially the same as that of the gel vehicle have been advantageously used in clear gel toothpastes to provide good cleaning and polishing characteristics without seriously affecting the clarity of the gel vehicle. In addition, the invention provides particular visible agglomerates of hard abrasive sub-particles held together by a binding agent that, when dispersed in a clear gel toothpaste vehicle having an invisible polishing ingredient, provide significantly greater cleaning and polishing characteristics as well as an attractive speckling effect without clouding or opacifying the clear gel vehicle as would occur if the hard abrasive subparticles were incorporated directly into the clear toothpaste and without significantly increasing the abrasiveness of the formulation to exposed dentin tissue.

The visible agglomerates of the invention are substantially insoluble in the gel vehicle or matrix and maintain their physical integrity during blending with the toothpaste base. When subjected to mechanical agitation such as during toothbrushing the agglomerates are reduced by disintegration or deformation to a substantially impalpable form that is easily rinsed from the mouth.

For use in the visible agglomerates of the invention suitable hard abrasive particles should preferably have a Moh hardness of at least 5 and a particle size between about 0.1 and 10 microns although larger particles could be used successfully. Representative of suitable materials are zirconium silicate ($ZrSiO_4$), silica (sand, quartz) ground glass (calcium silicate), silicon carbide (grit), pumice, alumina, ilmenite ($FeTiO_3$), $CeO_2$, $Fe_2O_3$, (hematite), $SnO_2$, Topaz (aluminum hydroxy fluoro silicate), and $TiO_2$. Any of the many other mineral substances, such as hard silicate minerals, found in nature or manufactured, which have the foregoing specified hardness and particle size requirements, can be used in accordance with the invention. Visible agglomerates in accordance with the invention containing sub-particles of zirconium silicate as the hard abrasive material have been found to provide a particularly advantageous cosmetic effect with no significant increase in dentin abrasion and are, preferred.

Particularly advantageous aesthetic effects can be obtained by using agglomerates of hard abrasive subparticles which have a refractive index within the range of about 1.5 to 2.7, particularly 1.7 to 2.2. When these special agglomerates are dispersed in a clear gel matrix having a refractive index from about 1.4 to 1.5, there results unique light reflectance effects including sharp delineation of the boundaries of the three-dimensional discrete agglomerates against a contrasting gel matrix forming a sparkling clear dispersion. In contrast, various softer materials may tend to provide agglomerates with a more indistinct or obscure appearance. The preferred zirconium silicate subparticles have a refractive index of about 1.9 to 2.1 and are particularly attractive in the clear gel formulation.

The preparation of hard abrasive particles suitable for use in accordance with the invention can be accomplished by conventional techniques well known in the art. For example, the preferred zirconium silicate sub-particles can be obtained from zirconium silicate ore by a ball milling technique in which a cylindrical or conical shell rotates on a horizontal axis which is charged with a grinding medium such as balls of steel, flint, or porcelain. The grinding is accomplished by the tumbling action of the balls on the material to be ground. Particles of zirconium silicate which are ball milled have relatively smooth surfaces and good cleaning and polishing action. The desired size particles can be isolated by conventional screening techniques.

Zirconium silicate, and other hard abrasive particles, may also be prepared by hammer milling. Hammer mills utilize a high speed rotary shaft having a plurality of hammers or beaters mounted thereon. The hammers may be T-shaped elements, bars, or rings fixed or pivoted in a housing containing grinding plates or liners. The grinding action results from the impact between the material being milled and the moving hammers. When zirconium silicate is milled by an attrition technique such as hammer milling, relatively rough, jagged particles are produced which have good cleaning and polishing action. Mixtures of ball and hammer milled zirconium silicate may also be advantageously used in this invention.

In accordance with the invention, a plurality of hard abrasive sub-particles having a mean particle diameter between about 0.1 and 10.0 microns, or larger depending on the degree of grittiness desired in the final toothpaste, are joined together by a binding agent to form a lesser plurality of visible agglomerates having abrasive properties which are subsequently incorporated into a toothpaste. To obtain the desired speckled effect, the agglomerate particles should contrast with the color of the toothpaste. Accordingly, the agglomerates can be white or colored, depending on the color of the toothpaste.

The visible abrasive agglomerates in accordance with the invention, can vary in particle size from about 100 to about 1,000 microns, preferably between 200 and 500 microns and are individually macroscopically visible both on the surface and in the interior of a suitable clear gel toothpaste formulation. From about 0.5 to about 10.0 percent, preferably from 1 to 5 percent by weight of the new abrasive agglomerate particles can be added to and dispersed in a suitable toothpaste formulation to obtain the desired cleaning, polishing and aesthetic characteristics, although lesser or greater amounts may be used depending on the effect desired. The agglomerates can include binding agent and hard abrasive material in a weight ratio between 1:9 and 9:1.

Suitable binding agents for use in accordance with the invention include the broad class of resins, gums, gels, waxes, polymers, etc. known in the art as binders. A preferred group of binders in accordance with the invention are natural and synthetic materials classified as thermoplastic, i.e. materials that soften and are rendered moldable when heated. Representative of this latter group are ethylenically unsaturated polymers such as polyethylene, polyvinyl chloride, polyvinyl acetate, copolymers of polyvinyl chloride and vinyl alcohol, vinyl acetate and vinylidene chloride, polystyrene, polymethylstyrene; synthetic rubbers such as styrenebutadiene copolymers and copolymers of alpha methyl styrene and vinyl toluene; polymethacrylates, such as polymethyl methacrylate, polyethyl methacrylate, polyisopropyl methacrylate, polyisobutyl methacrylate; polyacrylates; polyamides such as nylon; cellulosics such as acetates and butyrates, polycarbonates; phenoxys such as polymers of bisphenol-A and epichlorohydrin; polymers of monomers containing at least 2 polymerizable groups that are initially rendered moldable when heated and subsequently harden when heating is continued, such as polyallyl methacrylate and the polymers of the di-esters of methacrylic acid and ethylene glycol; coumarone-indene resins, polyethylene glycols, and natural waxes such has carnauba and paraffin, and mixtures of the foregoing materials.

In accordance with a specific aspect of the present invention, advantageous results can be obtained by utilizing a thermoplastic binding agent having a molecular weight between about 500 and about 20,000 and preferably at least about 1000. The hardness, expressed as tenths of mm needle penetration 100 grams/5 sec/25°C(ASTMD1321) of preferred materials in this class is typically between about 1 and 15 although harder grades can be used if not objectionable in the final toothpaste. The following table lists the properties of thermoplastic binding agents representative of this preferred class.

| Resin | Average Molecular Weight | Softening Point (Approx.) | Hardness | Specific Gravity | Average Viscosity CP |
|---|---|---|---|---|---|
| polyethylene[1] | 2,000 | 105°C. | 3.5 | 0.92 | 200(140°C) |
| " | 2,200 | 107°C. | 3.0 | 0.92 | 220 " |
| " | 3,500 | 116°C. | 1.0 | 0.93 | 350 " |
| " | 5,000 | 109°C. | 2.5 | 0.92 | 4000 " |
| " | 1,500 | 102°C. | 7.5 | 0.91 | 145 " |
| " | 2,000 | 96°C. | 9.5 | 0.91 | 230 " |
| oxidized polyethylene[2] | 1,800 | 104°C. | 4.0 | 0.94 | 320(125°C) |
| " | 3,000 | 106°C. | 3.0 | 0.94 | 1200 " |
| Polyamide[3] | 6,000–9000 | 110°C | 4 | 0.98 | 2200(150°C) |
| " | " | 95°C | 15 | 0.98 | 1100 (") |
| " | " | 110°C | 3 | 0.98 | 3800 |
| Alpha methyl Styrene-vinyl toluene copolymer[4] | 1,000 | 100°C | — | — | 3500(140°) |

[1]Available from Allied Chemical Company under the trademark A-C polyethylene grades 6, 6A, 7, 7A, 8, 8A, 615, 617, 617A, G-201, and 400.

[2]Available from Eastman Chemical Products, Kingsport Tenn. under the trademark EPOLENE. These materials are emulsifiable and have both an acid value and saponification number of 9–10. Similar materials are available from Allied Chemical Company under the trademark A-C polyethylene grades 656, 629, 655 and 680.

[3]Produced from ethylene diamine in accordance with U.S. patent number 2,379,413. Available from the Chemical Division of General Mills Co., Kankakee, Ill. under the trademark Versamid grades 930, 940 and 950.

[4]Available from Picco Resin Company, Clairton, Pa., under the trademark Piccotex 100.

The foregoing materials are non-toxic, tasteless, and do not attack the material from which the packaging tube for the toothpaste is constructed (usually aluminum or lead).

Visible abrasive agglomerate particles in accordance with another aspect of the invention can be produced by first dry blending a suitable binding agent in powder form, with the hard abrasive subparticles and a suitable coloring agent if coloring is desired. The weight ratio of binding agent to hard abrasive material can vary from about 1:9 to 9:1. The dry mixture is then placed in a heating apparatus and uniformly heated and mixed until the binding agent material softens and begins to agglomerate. A suitable heating apparatus should provide substantially uniform heat to the dry mixture to avoid hot spots and actual melting of the binding agent material. Representative of suitable heating apparatus are heated fluidized sand baths and oil baths.

When the binding agent material begins to agglomerate i.e., before it becomes molten, it is removed from the heat source and cooled to a temperature below it softening point while still being mixed. The cooled mass is then ground to particulate form in a suitable apparatus such as a ball or hammer mill. Solid carbon dioxide can be added during the grinding step in order to prevent the temperature from rising above the softening point of the binding agent material from the heat generated during grinding. The resulting agglomerated particles typically are irregularly shaped. The desired size particles are isolated by screening the particulate material through appropriate sieve screens. Generally, the portion of the particulate material passign through a 20 mesh (U.S. sieve series) and retained by a 60 mesh or 80 mesh screen (U.S. sieve series) is preferred for use in accordance with the invention.

Alternatively, the thermoplastic binding agent can be heated until molten and subparticles of hard abrasive material can be uniformly blended into the molten mass. The molten mass can be subsequently solidified by cooling, subjected to grinding, and screened to isolate agglomerates in the desired size range. The foregoing alternative technique is advantageous to use with binding agent materials having a sharp melting point such as carnauba wax and paraffin wax.

The agglomerated particles produced by the foregoing procedures are usually irregularly shaped and have a mean particle size between about 177 or 250 and 840 microns. Of course, any segment of this size range of particles can be further isolated for a particular application. Agglomerated particles having a mean particle diameter between about 250 and 420 microns are particularly advantageous.

In further accordance with the invention, novel abrasive agglomerates that are particularly suitable for incorporation into clear gel dental vehicles to enhance their cleaning and polishing characteristics and to provide an aesthetically attractive speckling effect, are produced by the following procedure.

Particles of thermoplastic binding agent material of the size range desired for the finished agglomerates and subparticles of a hard abrasive material in the size range between about 0.1 and 10 microns are dry mixed in a suitable vessel. THe dry mixture usually comprises from about 10 to 90 percent by weight binding agent and from about 90 to 10 percent by weight hard abrasive material. The vessel containing the mixture is then placed in an appropriate heating apparatus and rotated at a speed sufficient to cause the mixture to tumble while being heated. Preferably, the mixture is heated to a temperature slightly below the softening point of the binding agent and tumbled for about 15 minutes while being heated at that temperature. Care should be taken to insure that the particles of binding agent material do not agglomerate among themselves or become molten.

The dry mixture is continuously rotated and heated until substantially all of the subparticles are embedded in the softened surface of the particles of binding agent material. When the surface of the particle of binding agent are substantially free from loose, unbound subparticles, heating is terminated and the particles are cooled. The agglomerated particles can then be screened to remove any fines that may be present and subsequently re-heated and tumbled for another 15 minutes.

The agglomerated particles produced by the foregoing procedure generally retain the configuration of the binding agent particles initially charged to the heating vessel. Usually the particles of binding agent material are ellipsoidal or spherical in shape with rounded as opposed to jagged edges.

The new agglomerates have a surface crust comprising subparticles of hard abrasive material dispersed in binding agent and primarily a solid inner core of binding agent material. From about 5 to 10 percent of the agglomerates produced by this process are substantially the same as the solid core agglomerates, except that they have a hollow inner core. The proportion of hollow inner core agglomerates produced by the foregoing method may be raised by increasing the heating time for the binding agent, hard abrasive mixture.

Further, up to about 50% by weight of the agglomerates are usually in the form of small particles of binding agent with hard abrasive subparticles embedded therein, clustered together to form clump-like agglomerates in the desired size range. The small particles making up the clump-type agglomerates are apparently fines of binding agent material originally present in the charge of binding agent to the heating vessel.

It should be noted that although the foregoing procedure typically produces a mixture of solid core, hollow core, and clump-type agglomerates, variations in the process conditions and/or particle size of the initial binding agent feed can result in greater or lesser amounts of any one of the different types of agglomerates. According to this aspect of the invention the visible abrasive agglomerates can be solely in the form of either solid core, hollow core of clump-type agglomerates or a mixture of any two or all three types in any proportions. FIGS. 1, 2 and 3 of the drawing show the various types of agglomerates produced by the foregoing method.

The photomicrographs were made with a Cambridge scanning election microscope using reflected light on the scale indicated.

Figure 2:
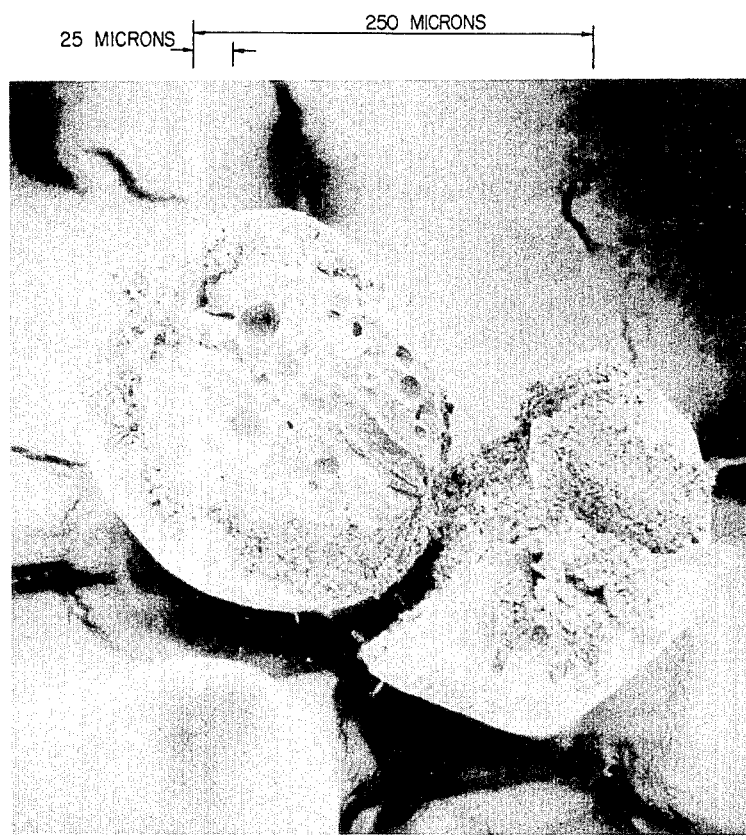
FIG. 2 is a photomicrograph (400 ×) showing the interior of a solid inner core agglomerate according to the invention.

The inner core of both the solid and hollow core agglomerates are substantially free from subparticles of abrasive material i.e., the subparticles of hard abrasive material are concentrated in a crust of binding agent extending from the surface of the agglomerate to the inner core. The crust of binding agent is a fused material, while the solid central core is distinct and in the same physical condition as the original binding agent material. As shown in FIG. 2, microscopic examination of disected solid core particles shows a distinct line of separation between the fused crust and the solid core of binding agent material. The solid or hollow inner core of the agglomerates usually has a diameter of about 50 – 95% of the agglomerate diameter. Typically, an agglomerate 400 microns in diameter would contain virtually all of the hard abrasive material in an outer shell of binding agent about 10 to about 100 microns thick. The inner core of the 400 micron size agglomerate would typically be from about 200 to 380 microns in diameter and virtually free of hard abrasive material.

Alternative methods and binding agents can be used to make visible agglomerates of hard abrasiveness subparticles in accordance with the invention. For example, visible agglomerates of hard abrasive subparticles can be made by utilizing direct compression techniques well knonw in the tableting art. Suitable binding agents for agglomerating hard abrasive subparticles by the direct compression technique include gums such as gum acacia and gum tragacanth, gelatins, starches and polyethylene glycols. In the direct compression method for forming agglomerates, a mixture of binding agent and hard abrasive subparticles are compressed in a tableting press to produce a tablet. The tablet is subsequently broken down in a suitable grinding apparatus and screened to recover the desired range of particle sizes.

Further, agglomerates of hard abrasive subparticles can be produced by a wet granulation process wherein the subparticles of hard abrasive material are wetted with solvent solution of a suitable binding agent to form a wet mass which is subsequently forced through a screen having the desired size openings. The wet agglomerates formed are then dried by air or in an oven and further screened to isolate a specific size range of agglomerates. The wet granulation procedure can be used by itself to produce agglomerates or in combination with direct compression to form a tablet which can be subsequently broken down and screened to isolate agglomerates in the desired size range.

As previously mentioned, the new macroscopically visible abrasive agglomerates can be colored to contrast with the toothpaste. Any non-toxic dye of a suitable color can be used for this purpose. It is usually desirable to utilize a dye or pigment that is approved for drug and cosmetic use (D&C) or food, drug and cosmetic use (FD&C).

Representative of suitable dyes are the following: D&C Red numbers 2, 3, 6, 7, 8, 9, 10, 11, 12, 13, 19, 21, 30, 31, 36 and 37, D&C Blue number 1, FD&C Blue numbers 1 and 2, FD&C Red numbers 1, 2 and 3, cosmetic green oxide and cosmetic red oxide. Pigments, known as lakes, of the foregoing dyes are also very suitable for use in coloring the new abrasive agglomerates. A pigment is generally defined as a finely powdered insoluble colored material e.g., a dye supported on a carrier, that is dispersed and suspended, as opposed to being dissolved in the medium to be colored.

The toothpaste formulations of the invention include clear gel dental vehicles of desired consistency which are extrudable from an aerosol container or a collapsible tube (for example aluminum or lead). The clear gel vehicle contains liquids and solids. In general, the liquids in the dental vehicle will comprise chiefly water, glycerine, aqueous solutions of sorbitol, propylene glycol, polyethylene glycol 400, etc., including suitable mixtures thereof. It is usually advantageous to employ a mixture of both water and a humectant or binder such as glycerine or sorbitol. The total liquid content will generally be about 20 to 75 percent by weight of the formulation. It is preferred to use also a gelling agent such as the natural and synthetic gums and gum-like materials, for example, Irish moss, gum tragacanth, methyl cellulose, polyvinylpyrrolidone, hydrophilic colloidal carboxyvinyl polymers, such as those sold under the trademark Carbopol 934 and 940 and synthetic silicated clays such as those sold under the trademark Laponite CP and Laponite SP. These grades of Laponite have the formula[$Si_8Mg_{5.1}Li_{0.6}H_{7.6}O_{24}$] $0.6^-$ $Na^+0.6$. The solid portion of the vehicle is usually present in an amount up to about 10 percent preferably about 0.2 to 5 percent by weight of the formulation.

As previously mentioned, clear gel dental vehicles include a suitable abrasive material. Suitable abrasive materials are those having a refractive index close to that of the gel vehicle e.g. 1.4–1.5, which is necessary in order to maintain clarity, and include silica xerogels and metallic salts of aluminosilicate complexes. The amount of invisible abrasive material in the clear gel vehicle can be from about 5 to 50 percent by weight preferably between 10 and 20 percent by weight.

Silica xerogels are synthetic aggregated, amorphous, porous silica materials having an average particle diameter of between about 2 and 20 microns, preferably between about 3 and 15 microns, and generally a surface area of at least about 300, and up to about 600 to 800 square meters per gram. A suitable silica xerogel is available from Grace Davison Chemical Company under the trade name Syloid 63. This material has an average particle diameter of about 8–10 microns. Other suitable silica xerogels include Syloid 65 (average particle diameter of about 5 microns). Syloid 73 (average particle diameter of about 5 microns), and Syloid 72 and 74 all of which are available from the Grace Davison Chemical Company. The silica xerogels typically have a refractive index of about 1.46. Other suitable silica materials are available from the Monsanto Chemical Company under the trademark Santocel and Santocel 100.

The abrasive material used in the clear gel vehicle of the toothpaste formulations of the invention can be a water insoluble complex metallic salt of aluminosilicate having a refractive index close to that of the gel vehicle. Representative of such materials are synthetic amorphous complex aluminosilicate salts of an alkali metal or alkaline earth metal in which silica is interbonded with alumina and which contains up to 3.3% by weight of the polishing agent of alumina, and in which the mole ratio of silica to alumina is at least about 45:1. The foregoing alumino silicate abrasives have a refractive index between about 1.44 – 1.47 and include up to about 20% by weight of moisture and up to about 10% by weight of alkali metal or alkaline earth metal oxide.

The complex aluminosilicate salt described above is typically a sodium or calcium salt, and forms a particularly desirable product. It is an amorphous powder which further has the property that when incorporated in a clear gel dental vehicle the particles thereof become invisible. Thus, a suitable particle size for the polishing ingredient is up to about 40 microns, preferably about 1–20 microns. The typical moisture content, measured by loss on ignition is about 5–20% by weight of the polishing ingredient and the typical content of alkali metal oxide such as sodium oxide or alkaline earth metal oxide such as calcium oxide is up to about 10%, generally about 0.3–2%, by weight. Typically, the agent has a loose bulk density of up to about 0.2g/cc, preferably about 0.07–0.12g/cc.

The alumina content of the salt is typically from about 0.1 to 3.3% by weight and the mole ratio of silica to alumina is typically about 45:1 to 1500:1 or more. Thus alumina is typically present in the polishing agent bound to silica in amount of 0.1–3.3% and silica is similarly present in amounts of at least about 70%, usually about 70–90% or more by weight of the polishing agent. It is also desirable that the complex aluminosilicate employed in the instant invention exhibit a pH in the range of 4–10 preferably between about 5 and 6.

Figure 1:
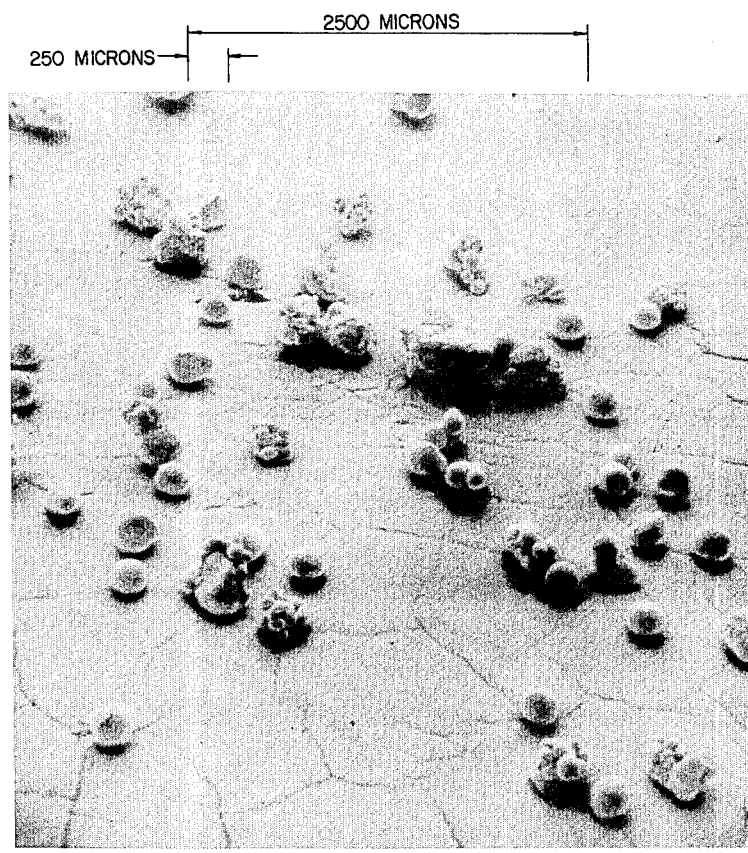
FIG. 1 is a photomicrograph (40 X) magnification showing an assortment of abrasive agglomerates in accordance with the invention.

The complex aluminosilicate salts appear to contain interbonded silica and alumina having Al-O-Si bonds as described by Tamele, "Chemistry of the Surface and the Activity of Alumina-Silica Cracking Catalyst", *Discussions of the Faraday Society*, No. 8, pages 270–279 (1950) and particularly at Page 273, FIG. 1, Curve 3 wherein the interaction between silica and aluminum ions is potentiometrically detected. Further literature describing this type of complex includes Milliken et al, "The Chemical Characteristics and Structure of Cracking Catalysts," *Discussions of the Faraday Society*, No. 8, pages 279–290 (1950) and particularly the sentence bridging pages 284 and 285.

Organic surface-active agents can be used in the toothpaste formulations of the present invention to assist in achieving thorough and complete dispersion of the instant compositions throughout the oral cavity and render the instant compositions more cosmetically acceptable. The organic surface-active material may be anionic, nonionic, ampholytic, or cationic in nature, and it is preferred to employ as the surface-active agent a detersive material which imparts to the composition detersive and foaming properties. It is preferred that the total amount of surface-active agent be about 0.05–5% by weight, preferably about 1–3%, of the dentifrice. Surface-active agents may include water-soluble sulfates of compounds having long chain alkyl radicals (e.g., chains of 10 to 18 carbon atoms). One preferred material is a long chain fatty acid monoglyceride sulfate, such as the sodium salt of hydrogenated coco fatty acid monoglyceride sulfate used alone or in combination with sodium lauryl sulfate. Other suitable materials are the fatty acid amides of amino acids such as sodium N-lauroyl sarcosinate and olefin sulfonates containing an olefinic group of from 8 to 25 carbon atoms.

Various other materials may be incorporated in the dentifrice formulations of the invention. Examples thereof are coloring agents or dyestuffs, preservatives, silicones, chlorophyll compounds, ammoniated materials such as urea, diammoniumphosphate and mixtures thereof, and other constituents. These adjuvants are incorporated in the instant compositions in amounts which do not substantially adversely effect the properties and characteristics desired and are selected and used in proper amount depending upon the particular type of preparation involved.

The compositions of the present invention, may also contain a fluorine-containing compound having a beneficial effect on the care and hygiene of the oral cavity, e.g., diminution of enamel solubility in acid and protection of the teeth against decay. Examples thereof include sodium fluoride, stannous fluoride, potassium fluoride, potassium stannous fluoride ($SnF_2$—KF), potassium fluorozirconate, sodium hexafluorostannate, stannous chlorofluoride, and sodium monofluorophosphate. These materials, which dissociate or release fluorine-containing ions suitably may be present in an effective but non-toxic amount, usually within the range of about 0.1 to 1% by weight, based on the water soluble fluorine content thereof. Sodium fluoride, stannous fluoride, and sodium monofluorophosphate are particularly preferred, as well as mixtures thereof.

Antibacterial agents may also be employed in the oral preparations of the instant invention to provide a total content of such agents of up to about 5% by weight. Typical antibacterial agents include $N^1$-(4-chlorobenzyl)-$N^5$-(2,4-dichlorobenzyl) biguanide;
p-chlorophenyl biguanide;
4-chlorobenzhydryl biguanide;
4-chlorobenzhydrylguanylurea;
N-3-lauroxypropyl-$N^5$-p-chlorobenzylbiguanide;
1-(lauryldimethylammonium)-8-(p-chlorobenzyldimethylammonium) octane dichloride;
5,6-dichloro-2-guanidinobenzimidazole;
$N^1$-p-chlorophenyl-$N^5$-laurylbiguanide;
1,6-Di-p-Chlorophenyl Biguanidohexane
1,6,bis (2, Ethylhexy Biguanido) hexane
5,amino-1, 3-bis (2-ethylhexyl)-5-methylhexahydro pyrimidine;
and their non-toxic acid addition salts.

Synthetic finely divided pyrogenic silica such as those sold under the trademarks Cab-O-Sil M-5, Syloid 244, Syloid 266 and Aerosil D-200 may also be employed in amounts of about 1–20%, preferably 1–5%, by weight to promote thickening or gelling and to improve clarity of the dentifrice.

The taste of the new compositions may be modified by employing suitable flavoring or sweetening materials. Examples of suitable flavoring constituents include the flavoring oils, e.g. oils of spearmint, peppermint, wintergreen, sassafras, clove, sage, eucalyptus, marjoram, cinnamon, lemon and orange as well as sodium methylsalicylate. Suitable sweetening agents include sucrose, lactose, maltose, sorbitol, sodium cyclamate, perillartine and saccharine. Suitably, flavor and sweetening agents may together comprise from about 0.01 to 5% or more of the compositions of the instant invention. Additionally, the new dental formulations can be provided with the unusual, biting flavor of chloroform. Accordingly, instead of or in addition to the foregoing flavoring or sweetening materials, the new formulation can include up to about 5%, preferably between 1 and 5%, by weight of chloroform and chloroform flavoring.

It is desirable to adjust the pH of the toothpaste formulations to the range of about 3 to 9 using such acids as citric, acetic, chloropropionic, malonic, formic, furmaric, methoxyacetic, and propionic. Lower pH's than 3 are generally undesirable for oral use. When stannous ions are present, the pH is preferably lower than about 5. The preferred pH range is 3.5 to about 5.0 when stannous ions are present and about 4.5 to about 7.0 in the absence of stannous ions.

The following specific examples are further illustrative of the nature of the present invention but it is understood that the invention is not limited thereto. Toothpaste formulations are prepared in the usual manner, except as indicated, and all amounts and proportions are by weight except as otherwise indicated.

EXAMPLE 1

Colored abrasive agglomerates suitable for incorporation into various toothpaste formulations are prepared in accordance with the following procedure:

20 parts of a non-emulsifiable grade of polyethylene in particulate form having the following properties:

| | |
|---|---|
| Molecular weight | approx. 1500 |
| Softening Point | 102°C. |
| Hardness | 7.5 |
| Density g/cc | 0.91 |
| Viscosity cps. 140°C Brookfield | 145 | are dry mixed with 80 parts of zirconium silicate (Zr $SiO_4$) in particulate form having a mean particle diameter of 1 micron, and a Moh hardness of 8 and 1 part of FD&C Red number 2 aluminum lake pigment in a suitable vessel. The vessel containing the dry mix is heated in a suitable heating apparatus. The dry mix is stirred while being heated. When the softening point of the polyethylene binding agent is reached and before it becomes molten, the vessel is removed from the heating apparatus and cooled while still being stirred. The cooled mass is then ground to particulate form in a blender type apparatus and screened. The fraction passing through a 40 mesh screen (U.S. series) and retained by a 60 mesh screen is collected for use in accordance with the invention. The collected agglomerates have a distinctive red color, a mean diameter between about 250 and 420 microns and can be advantageously combined with various toothpaste vehicles to produce an aesthetically attractive speckled toothpaste having improved polishing and cleaning characteristics. If white particles are desired, the pigment ingredient can be left out of the foregoing formulation.

EXAMPLE 2

Example 1 is repeated using an oxidized polyethylene resin having a softening point of about 104°C and an average molecular weight of about 1800 as the binding agent. The weight ratio of binding agent to abrasive is 1:3.

EXAMPLE 3

Example 1 is repeated using a polyamide resin having a softening point of 110°C and an average molecular weight of between 6000 and 9000 as the binding agent. The weight ratio of binding agent to abrasive is 4:1.

EXAMPLE 4

Example 1 is repeated using an alpha methyl styrenevinyl toluene copolymer resin having a softening point of about 100°C and an average molecular weight of 1000 as the binding agent. The weight ratio of binding agent to abrasive is 1:7.

EXAMPLE 5

The procedure of Example 1 is substantially repeated using natural carnauba wax having a softening point between 81°C and 86°C as the binding agent. The weight ratio of binding agent to abrasive is 1:1.

The Example 1 procedure is varied by heating the carnauba wax until it is molten and blending the subparticles of zirconium silicate into the molten mass, followed by cooling, grinding and screening.

EXAMPLE 6

Figure 3:
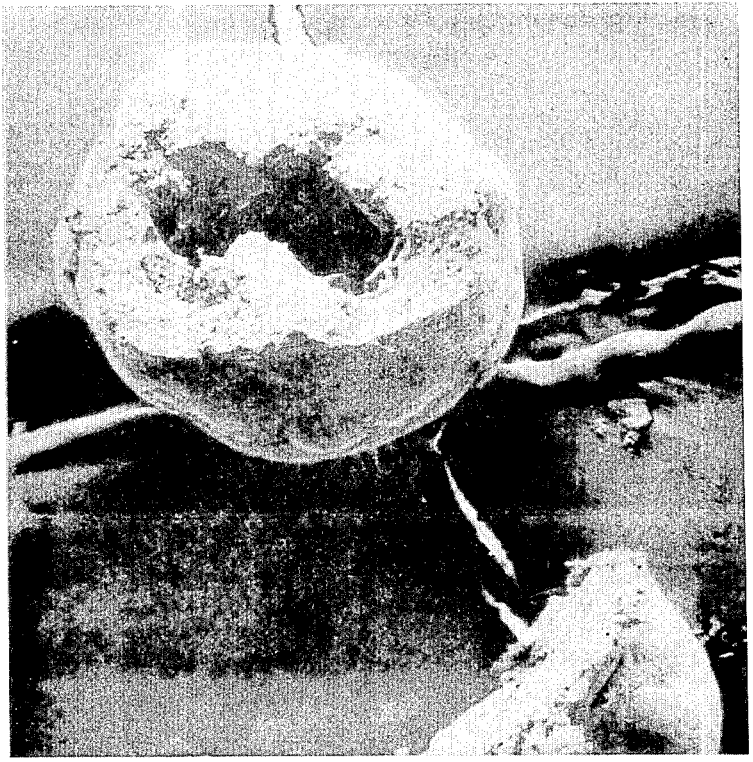
FIG. 3 is a photomicrograph (400 ×) showing the interior of a hollow inner core agglomerate according to the invention.

20 parts of polyethylene binding agent according to Example 1, having a particle size between 250 and 420 microns are dry mixed with 80 parts of zirconium silicate particles having a particle size distribution between 0.5 microns and 3 microns in a suitable vessel. The vessel containing the mixture is then placed in a fluidized sand bed, heated to 105°F and rotated at 8RPM causing the mixture to tumble. The mixing is heated while being tumbled until the zirconium silicate particles are substantially captured beneath the surface of the polyethylene particles. The agglomerates are then cooled and collected. The particles produced by this procedure have a smooth surface with a crust of zirconium silicate particles and polyethylene surrounding a core of solid polyethylene as shown in FIGS. 1 and 2. Some of the agglomerates produced by the foregoing procedure have a hollow core (see FIG. 3) as opposed to the more common core of solid polyethylene (see FIG. 2) and some appear to be clumps of agglomerated small particles as shown in FIG. 1.

EXAMPLE 7

Example 6 is repeated using an oxidized polyethylene resin having softening point of about 106°C and an average molecular weight of 3,000 as the binding agent. The weight ratio of binding agent to abrasive is 1:8.

EXAMPLE 8

Example 6 is repeated using an alpha methyl styrenevinyl toluene copolymer resin having a softening point of about 100°C and an average molecular weight of 1,000. The weight ratio of binding agent to abrasive is 1:6.

EXAMPLE 9

Example 6 is repeated using natural carnauba wax having a softening point between 81°C and 86°C as the binding agent. The weight ratio of binding agent to abrasive is 1:9.

All of the foregoing examples produce abrasive agglomerates suitable for incorporation into a variety of toothpaste formulations. Of course, the color of the agglomerates can be varied by using other suitable coloring materials. Suitable abrasive agglomerates can be produced by the procedures of Examples 1 and 6 using as the hard abrasive material powdered alumina (mean particle size 6 microns, Moh hardness 8), powdered silica (mean particle size 5 microns, Moh hardness 5) powdered $SnO_2$, (mean particle size 3 microns, Moh hardness 6), powdered feldspar ($KALSi_3O_8$, mean particle size 6 microns, Moh hardness 6) milled topaz (mean particle size 8 microns, Moh hardness 8), and ground pyrex glass (mean particle size 10 microns, Moh hardness 7).

Specific toothpaste formulations with which abrasive agglomerates produced in accordance with foregoing examples can be combined, are described in the following examples. However, it should be appreciated that any of the abrasive agglomerates can be combined with any suitable toothpaste base to produce a speckled toothpaste having improved cleaning and polishing characteristics.

EXAMPLE 10

A transparent toothpaste having the following composition is formulated by the usual techniques.

| Components | Parts |
| --- | --- |
| Glycerine | 25.00 |
| Sodium carboxymethylcellulose | 0.70 |
| Sodium saccharin | 0.17 |
| Sodium benzoate | 0.50 |
| Sorbitol (70% aqueous solution) | 44.83 |
| Dye Solution (Red) | 0.80 |
| Water | 3.00 |
| Sodium aluminom silicate | 16.00 |
| Syloid 244 | 5.00 |
| Flavor | 1.00 |
| Sodium lauryl sulfate | 2.00 |
| Chloroform | 1.00 |

The sodium aluminosilicate employed is a complex having a refractive index of 1.46, a moisture content of about 6 percent, an average particulate size of about 35 microns and a sieve loose bulk density of about 0.07g/cc.

2 parts by weight of the abrasive agglomerates produced by the procedure of Example 6 are added to, and uniformly blended with the foregoing formulation. The resulting toothpaste has a pleasing speckled appearance and substantially improved cleaning and polishing characteristics relative to the same formulation without the agglomerates, without a significant increase in dentin abrasion. Further, the agglomerates do not break down to a significant degree when blended into the gel base, and are substantially impalpable in the mouth during toothbrushing.

Similarly, two parts by weight of the agglomerates of any one of examples 7 to 9 can be incorporated into the foregoing clear gel to produce a toothpaste in accordance with the invention.

EXAMPLE 11

The following visually clear toothpaste is prepared:

| Components | Parts |
| --- | --- |
| Sorbitol (70% aqueous solution) | 75.0 |
| Glycerine | 25.0 |
| Laponite SP | 2.03 |
| Sodium N-lauroyl sarcosinate | 2.0 |
| Sodium saccharin | 0.1 |
| Aerosil D200 | 3.0 |
| Sodium aluminosilicate | 16.0 |
| Flavor | 1.0 |
| Color | 1.0 |
| Water | 20.0 |

3 parts by weight of the white abrasive agglomerates of Example 1 are uniformly dispersed in the foregoing formulation to produce a dentifrice product in accordance with the invention.

Similarly, three parts by weight of the abrasive agglomerates according to any one of Examples 2 to 5 can be incorporated into the foregoing clear gel toothpaste formulation to produce a toothpaste in accordance with the invention.

EXAMPLE 12

2 parts by weight of the abrasive particles of Example 9 are dispersed in the clear gel dental vehicle of Example 10 with Syloid 74 substituted for the sodium aluminosilicate abrasive material.

The specific formulations of the foregoing examples are aesthetically attractive and functionally exhibit improvement in properties desirable for oral hygiene such as in the stain removing or polishing characteristics relative to the same toothpaste before the abrasive agglomerates are added, without exhibiting significantly greater abrasion to the dentin tissues of the teeth or adversely effecting the visual clarity of the clear gel vehicle. Of course, the stain removing and polishing characteristics of the toothpaste formulations containing the new abrasive agglomerate particles varies according to the type of hard abrasive used, its concentration in the agglomerate particles and the concentration of the agglomerate particles in the toothpaste. However, such formulations can be prepared as desired to possess significant improvement in stain removal and polishing without a significant increase in dentin abrasion. The presence in a clear gel toothpaste of 2 percent by weight of abrasive particles in accordance with the invention can raise the stain removal ability of a toothpaste from about 30 – 40 percent to as high as 60 – 70 percent. The polishing ability of the dentifrice usually improves a corresponding amount and abrasiveness to human dentin is not appreciably changed.

Although the foregoing specific examples include preferred and typical formulations, they should not be taken as limitations on the invention. Accordingly, reference should be made to the following claims in determining the full scope of the invention.

We claim:

1. Macroscopically visible abrasive agglomerates having dental cleaning and polishing characteristics and suitable for incorporation into a clear gel dental vehicle, each of said agglomerates having a particle size from 100 to 1,000 microns, said agglomerates consisting essentially of an outer crust including a plurality of hard abrasive subparticles having a Moh hardness of at least 5 and a mean particle diameter between 0.1 and 10 microns selected from the group consisting of zirconium silicate, silica, $SnO_2$, feldspar, topaz, calcium silicate, silicon carbide, pumice, alumina, ilemite, hematite, and titanium dioxide and a binding material selected from the group consisting of thermoplastic polymer and wax and an inner core substantially free of said subparticles, said subparticles and said binding agent material being present in a weight ratio of from about 1:9 to about 9:1.

2. Abrasive agglomerates according to claim 1 wherein said inner core is hollow.

3. Abrasive agglomerates according to claim 1 wherein said inner core consists essentially of binding agent material.

4. Abrasive agglomerates according to claim 1 wherein said subparticles have a mean diameter between 0.1 and 10 microns.

5. Abrasive agglomerates according to claim 4 wherein said hard abrasive material is zirconium silicate.

6. Abrasive agglomerates according to claim 1 wherein said binding agent is low molecular weight polyethylene.

7. Abrasive agglomerates according to claim 1 wherein the diameter of said inner core is from 50 to 95 percent of the diameter of said abrasive agglomerate.

8. Process for producing the macroscopically visible abrasive agglomerates as defined in claim 6 comprising dry mixing from 10 to 90 parts of said low molecular weight polyethylene having a mean diameter from 100 to 1,000 microns with 10 to 90 parts of said hard abrasive subparticles, rotating said mixture at a speed sufficient to cause tumbling, heating said mixture to the softening point of said low molecular weight polyethylene while simultaneously rotating said mixture until said subparticles are captured in the surface of said low molecular weight polyethylene, cooling said mixture and isolating agglomerates of said mean diameter by screening.

* * * * *